(12) United States Patent
Hellberg et al.

(10) Patent No.: US 7,906,512 B2
(45) Date of Patent: *Mar. 15, 2011

(54) 3,6-SUBSTITUTED IMIDAZOL[1,2-B]PYRIDAZINE ANALOGS FOR TREATING ALLERGIC AND INFLAMMATORY DISEASES

(75) Inventors: Mark R. Hellberg, Arlington, TX (US); Steven T. Miller, Arlington, TX (US); Andrew Rusinko, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/720,808

(22) Filed: Mar. 10, 2010

(65) Prior Publication Data

US 2010/0168116 A1 Jul. 1, 2010

Related U.S. Application Data

(63) Continuation of application No. 11/330,590, filed on Jan. 12, 2006, now Pat. No. 7,713,975.

(60) Provisional application No. 60/643,386, filed on Jan. 12, 2005, provisional application No. 60/695,967, filed on Jul. 1, 2005.

(51) Int. Cl.
| | |
|---|---|
| *A01N 43/58* | (2006.01) |
| *A01N 43/60* | (2006.01) |
| *A01N 43/52* | (2006.01) |
| *A61K 31/50* | (2006.01) |
| *A61K 31/495* | (2006.01) |
| *A61K 31/501* | (2006.01) |
| *A61K 31/415* | (2006.01) |
| *C07D 487/00* | (2006.01) |
| *C07D 401/00* | (2006.01) |
| *C07D 403/00* | (2006.01) |
| *C07D 405/00* | (2006.01) |
| *C07D 409/00* | (2006.01) |
| *C07D 235/02* | (2006.01) |
| *C07D 403/02* | (2006.01) |

(52) U.S. Cl. ............... 514/248; 514/252.06; 514/393; 544/236; 544/238; 548/303.1

(58) Field of Classification Search ............. 514/248, 514/252.06, 393; 544/236, 238; 548/303.1
See application file for complete search history.

(56) References Cited

U.S. PATENT DOCUMENTS

2004/0067948 A1* 4/2004 Hallett ................. 514/248

FOREIGN PATENT DOCUMENTS

| WO | WO2004014382 A1 | 2/2004 |
| WO | WO2004085409 A3 | 10/2004 |

OTHER PUBLICATIONS

Charles L. Cywin, et al., Discovery and SAR of Novel [1,6]Naphthyridines as Potent Inhibitors of Spleen Tyrosine Kinase (SYK), Biorganic & Medicinal Chemistry Letters, 2003, pp. 1415-1418, vol. 13.

Justine Y. Q. Lai, et al., "Potent Small Molecule Inhibitors of Spleen Tyrosine Kinase (Syk)," Biorganic & Medicinal Chemistry Letters, 2003, pp. 3111-3114, vol. 13.

Reuben P. Siraganian, et al., "Protein Tyrosine Kinase Syk in Mast Cell Signaling," Molecular Immunology, 2001, pp. 1229-1233, vol. 38.

Jennifer A. Taylor, et al., "Activation of the High-Affinity Immunoglobulin E Receptor FcεRI in RBL-2H3 Cells is Inhibited by Syk SH2 Domains," Molecular and Cellular Biology, 1995, pp. 4149-4157, vol. 15, No. 8.

Noriyuki Yamamoto, et al., "The Orally Available Spleen Tyrosine Kinase Inhibitor 2-[7-(3,4-Dimethoxyphenyl)-imidazo[1,2-c]pyrimidin-5-ylamino]-nicotinamide Dihydrochloride (BAY 61-3606) Blocks Antigen-Induced Airway Inflammation in Rodents," The Journal of Pharmacology and Experimental Therapeutics, 2003, pp. 1174-1181, vol. 306, No. 3.

* cited by examiner

*Primary Examiner* — Sreeni Padmanabhan
*Assistant Examiner* — Sarah Pihonak
(74) *Attorney, Agent, or Firm* — Patrick M. Ryan

(57) ABSTRACT

Methods for treating an allergic or inflammatory disease or other Syk-mediated disease or Syk-mediated condition characterized by administering a composition which contains a therapeutically effective amount of a 3,6-substituted imidazol[1,2-b]pyridazine compound.

8 Claims, No Drawings

3,6-SUBSTITUTED IMIDAZOL[1,2-B]PYRIDAZINE ANALOGS FOR TREATING ALLERGIC AND INFLAMMATORY DISEASES

This application is a continuation of U.S. Ser. No. 11/330,590, filed Jan. 12, 2006, which claims priority to U.S. Provisional Applications, U.S. Ser. Nos. 60/643,386, filed Jan. 12, 2005, and 60/695,967 filed Jul. 1, 2005.

BACKGROUND OF THE INVENTION

1. Field of the Invention

The present invention relates to the treatment of allergic or inflammatory diseases or other Syk-mediated diseases or conditions. More particularly, the present invention relates to the topical or systemic administration of certain 3,6-substituted imidazol[1,2-b]pyridazine analogs for the treatment of such diseases or conditions.

2. Description of the Related Art

Syk is a tyrosine kinase that plays a critical role in mast cell degranulation, eosiniphil activation, lipid mediator synthesis and cytokine production. Accordingly, Syk kinase is implicated in various inflammatory and allergic disorders in particular asthma.

It has been shown that Syk binds to the phosphorylated gamma chain of the high affinity IgE receptor (Fcε RI) signaling via N-terminal SH2 domains and is essential for downstream signaling [Taylor et al, Molecular and Cellular Biology 1995; 15:4149-4157]. Syk kinase is important in the intracellular propagation of signaling following the crosslinking of the high affinity IgG receptor (FcγRI) by IgG. Since the mediators released as the results of Fcε RI and FcγRI are responsible at least in part for adverse effects associated with allergic responses or inflammation, compounds that inhibit Syk kinase may be effective in inhibiting those adverse effects [Sirganian et. al. Molecular Immunology 2002, 38:1229-1233].

The term "Syk-mediated disease" or "Syk-mediated condition", as used herein, means any disease or other deleterious condition in which Syk protein kinase is known to play a role. Such conditions include, without limitation, inflammation and allergic disorders, especially asthma.

As taught in WO 2004/014382 (Rigel Pharmaceuticals) certain 2,4-pyridinediamine compounds have Syk kinase inhibitory activity. Lai et. al. describe a series of oxindoles having Syk kinase activity [Biorganic and Medicinal Chemistry Letters 2003, 13:3111-3114. Cywin et. al. describe the activity of a series of [1,6]naphthyridine compounds that inhibit Syk kinase [Biorganic and Medicinal Chemistry Letters 2003, 13:1415-1418]. Yamamoto et. al. describe an orally available imidazo[1,2,c]pyrimidine Syk kinase inhibitor [Journal of Pharmacology and Experimental Theapeutics 2003, 306:1174-1181]. WO2004/085409 discloses 5-substituted 2,3-diaminopyrazines.

SUMMARY OF THE INVENTION

The present invention provides a method for treating an allergic or inflammatory disease or other Syk-mediated disease or Syk-mediated condition characterized by administering a formulation which contains a therapeutically effective amount of a 3,6-substituted imidazol[1,2-b]pyridazine compound of formula (I) or a pharmaceutically acceptable salt thereof. The compounds of formula (I) have Syk kinase inhibitory activity. In one embodiment, the compounds of formula (I) are administered topically to treat an allergic or inflammatory disease or other Syk-mediated disease or Syk-mediated condition of the eye, ear or nose. In a preferred embodiment, the compounds of the present invention are used to treat an allergic eye disease selected from the group consisting of allergic conjunctivitis; vernal conjunctivitis; vernal keratoconjunctivitis; and giant papillary conjunctivitis.

DETAILED DESCRIPTION OF THE INVENTION

The 3,6-substituted imidazol[1,2-b]pyridazine compounds useful in the methods of the present invention are defined by formula (I):

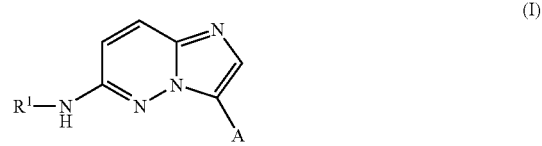

wherein:
A=aryl or heteroaryl optionally substituted by F, Cl, Br, $C_1$-$C_6$ alkyl, $OR^2$, or $OCF_3$;
$R^1$=H, $C_1$-$C_6$ alkyl, heterocyclyl, or $(CH_2)_n$—X;
n=1-4;
X=aryl, heteroaryl, $OR^5$ or $NR^3R^4$; and
$R^2$, $R^3$, $R^4$, $R^5$ independently=H or $C_1$-$C_6$ alkyl.

According to a preferred embodiment of the present invention, a compound of formula (I), or a pharmaceutically acceptable salt thereof, is topically administered to the eye. Examples of pharmaceutically acceptable salts of the compounds of formulas (I) include, but are not limited to, inorganic acid salts such as hydrochloride, hydrobromide, sulfate and phosphate; organic acid salts such as acetate, maleate, fumarate, tartrate and citrate; alkali metal salts such as sodium salt and potassium salt; alkaline earth metal salts such as magnesium salt and calcium salt; metal salts such as aluminum salt and zinc salt; and organic amine addition salts such as triethylamine addition salt (also known as tromethamine), morpholine addition salt and piperidine addition salt.

It is recognized that compounds of Formula (I) can contain one or more chiral centers. This invention contemplates all enantiomers, diastereomers, and mixtures thereof. In the above definitions, the total number of carbon atoms in a substituent group is indicated by the $C_i$-$C_j$ prefix, where the numbers i and j define the number of carbon atoms; this definition includes straight chain, branched chain, and cyclic alkyl or (cyclic alkyl)alkyl groups.

The term "aryl" refers to a monocyclic, bicyclic or tricyclic ring system having a total of five to fourteen ring members, wherein at least one ring in the system is aromatic and wherein each ring in the system contains 3 to 7 ring members. The term "aryl" may be used interchangeably with the term "aryl ring".

The term "heterocycle", "heterocyclyl", or "heterocyclic" as used herein means non-aromatic, monocyclic, bicyclic or tricyclic ring systems having three to fourteen ring members in which one or more ring members is a heteroatom, wherein each ring in the system contains 3 to 7 ring members.

The term "heteroaryl" refers to monocyclic, bicyclic or tricyclic ring systems having three to fourteen ring members wherein at least one ring in the system is aromatic, at least one ring in the system contains one or more heteroatoms, and wherein each ring in the system contains 3 to 7 ring members.

The term "heteroatom" means nitrogen, oxygen, or sulfur and includes any oxidized form of nitrogen and sulfur, and the quarternized form of any basic nitrogen. Also the term "nitrogen" includes a substitutable nitrogen of a heterocyclic ring. As an example, in a saturated or partially unsaturated ring having 0-3 heteroatoms selected form oxygen, sulfur or nitrogen, the nitrogen may be N (as in 3,4-dihydro-2H-pyrrolyl), NH (as in pyrrolidinyl) or NR (as in substituted pyrrolidinyl).

It is important to recognize that a substituent may be present either singly or multiply when incorporated into the indicated structural unit.

The compounds of this invention are commercially available (BioFocus Discovery, Ltd., United Kingdom).

The compounds of the present invention may be administered topically (i.e., local, organ-specific delivery) by means of conventional topical formulations, such as solutions, suspensions or gels for the eye and ear; nasal sprays or mists for the nose. The concentration of the 3,6-substituted imidazol[1,2-b]pyridazine compound of formula (I) in the formulations of the present invention will depend on the selected route of administration and dosage form, but will generally range from 0.00001 to 5% (w/v). For solutions intended for topical administration to the eye, the concentration of the 3,6-substituted imidazol[1,2-b]pyridazine compounds of formulas (I) is preferably 0.0001 to 0.5% (w/v). The topical compositions of the present invention are prepared according to conventional techniques and contain conventional excipients in addition to one or more 3,6-substituted imidazol[1,2-b]pyridazine compounds of formula (I). A general method of preparing eye drop compositions is described below:

One or more 3,6-substituted imidazol[1,2-b]pyridazine compounds of formula (I) and a tonicity-adjusting agent are added to sterilized purified water and if desired or required, one or more excipients. The tonicity-adjusting agent is present in an amount sufficient to cause the final composition to have an ophthalmically acceptable osmolality (generally about 150-450 mOsm, preferably 250-350 mOsm). Conventional excipients include preservatives, buffering agents, chelating agents or stabilizers, viscosity-enhancing agents and others. The chosen ingredients are mixed until homogeneous. After the solution is mixed, pH is adjusted (typically with NaOH or HCl) to be within a range suitable for topical ophthalmic use, preferably within the range of 4.5 to 8.

Many ophthalmically acceptable excipients are known, including, for example, sodium chloride, mannitol, glycerin or the like as a tonicity-adjusting agent; benzalkonium chloride, polyquaternium-1 or the like as a preservative; sodium hydrogenphosphate, sodium dihydrogenphosphate, boric acid or the like as a buffering agent; edetate disodium or the like as a chelating agent or stabilizer; polyvinyl alcohol, polyvinyl pyrrolidone, polyacrylic acid, to polysaccharide or the like as a viscosity-enhancing agent; and sodium hydroxide, hydrochloric acid or the like as a pH controller.

According to the present invention, the 3,6-substituted imidazol[1,2-b]pyridazine compounds of formulas (I) are useful for treating an allergic or inflammatory disease or other Syk-mediated diseases or Syk-mediated conditions. Such disorders include, but are not limited to, septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitiss, osteo and rheumatoid arthritis, ankylosing spondylitis, psoriatic arthritis, adult Still's disease, ureitis, Wegener's granulomatosis, Behcet's disease, Sjogren's syndrome, sarcoidosis, polymyositis, dermatomyositis, multiple sclerosis, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, transplant rejection, atopic dermatitis, vasculitis, ophthalmic allergic disorders, otic allergic disorders, nasal allergic disorders, rhinitis, sinusitis, reversible airway obstruction, adult respiratory distress syndrome, asthma, chronic obstructive pulmonary disease, and bronchitis.

In a preferred embodiment the compounds of formula (I) are useful in treating ophthalmic allergic disorders, including allergic conjunctivitis, vernal conjunctivitis, vernal keratoconjunctivitis, and giant papillary conjunctivitis; nasal allergic disorders, including allergic rhinitis and sinusitis; and otic allergic disorders, including eustachian tube itching.

For ocular disorders, the eye drops produced by the above method typically need only be applied to the eyes a few times a day in an amount of one to several drops at a time, though in more severe cases the drops may be applied several times a day. A typical drop is about 30 µl.

Certain embodiments of the invention are illustrated in the following examples.

Example 1

Topical Ophthalmic Solution Formulation

| Ingredient | Concentration (W/V %) |
| --- | --- |
| Compound of formula I | 0.1 |
| Dibasic Sodium Phosphate (Anhydrous), USP | 0.5 |
| Sodium Chloride, USP | 0.65 |
| Benzalkonium Chloride | 0.01 |
| Sodium Hydroxide, NF | q.s. pH 7.0 ± 0.2 |
| Hydrochloric Acid, NF | q.s. pH 7.0 ± 0.2 |
| Purified Water | q.s. 100 |

Example 2

Topical Ophthalmic Gel Formulation

| Ingredient | Concentration (W/V %) |
| --- | --- |
| Compound of formula I | 0.1 |
| Carbopol 974 P | 0.8 |
| Disodium EDTA | 0.01 |
| Polysorbate 80 | 0.05 |
| Benzalkonium Chloride, Solution | 0.01 + 5 xs |
| Sodium Hydroxide | q.s. pH 7.0 ± 0.2 |
| Hydrochloric acid | q.s. pH 7.0 ± 0.2 |
| Water for Injection | q.s. 100 |

Example 3

Syk Kinase Activity

In a final reaction volume of 25 µl, Syk (h) (5-10 mU) is incubated with 50 mM Tris pH 7.5, 0.1 EGTA, 0.1 mM Na$_3$VO$_4$, 0.1% β-mercaptoethanol, 0.1 mg/mL poly (Glu, Tyr) 4:1, 10 μM test agent, 10 mM MgAcetate and [γ-$^{33}$P-ATP] (specific activity approximately 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a Filtermat A and washed three times for 5 minutes in 75 mM phosphoric acid and once in methanol prior to drying and scintillation counting. Percent inhibition was calculated using the following formula:

% Control=((sample-mean no enzyme)/(mean plus enzyme-mean no enzyme))×100.

In the syk kinase inhibition assay described above, the compounds shown in Table 1 were tested and were found to inhibit syk kinase; the results are shown in Table 1 below.

TABLE 1

| Structure | % inhibition |
|---|---|
| 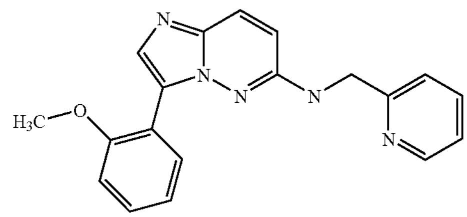 | 81 |
| 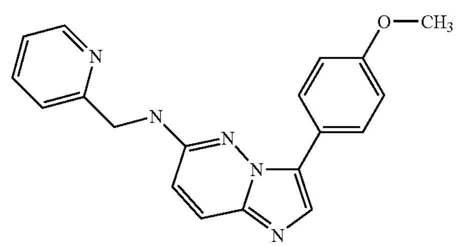 | 77 |
| 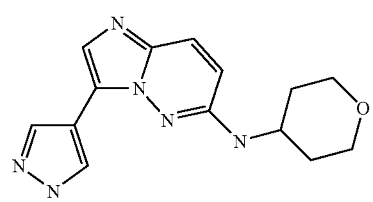 | 42 |
| 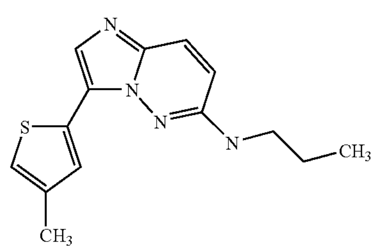 | 38 |
| 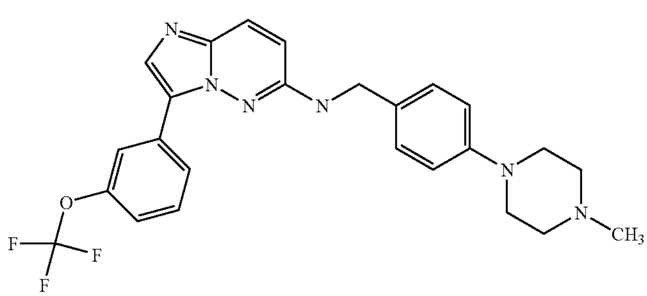 | 33 |

TABLE 1-continued

| Structure | % inhibition |
|---|---|
| 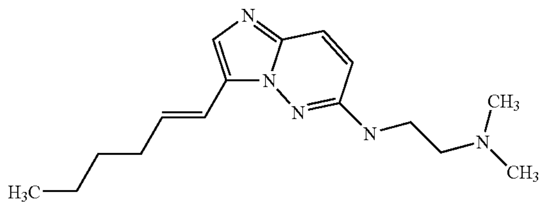 | 27 |
| 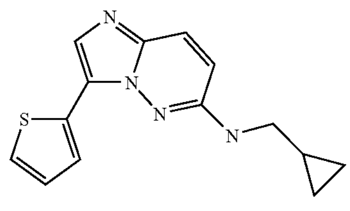 | 26 |
| 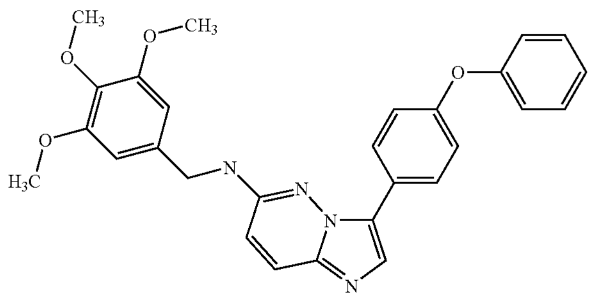 | 24 |
| 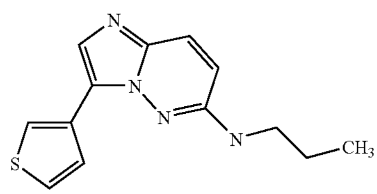 | 23 |

What is claimed is:

1. A method for treating an allergic or inflammatory disease or other Syk-mediated disease or Syk-mediated condition in a patient which comprises administering to the patient a composition comprising a therapeutically effective amount of a compound of the formula:

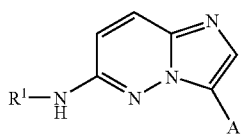

(I)

wherein:
A=aryl or heteroaryl optionally substituted by F, Cl, Br, $C_1$-$C_6$ alkyl, $OR^2$, or $OCF_3$;
$R^1$=H, $C_1$-$C_6$ alkyl, heterocyclyl, or $(CH_2)_n$—X;
n=1-4;
X=aryl, heteroaryl, $OR^5$ or $NR^3R^4$; and
$R^2$, $R^3$, $R^4$, $R^5$ independently=H or $C_1$-$C_6$ alkyl;

provided that the allergic or inflammatory disease or other Syk-mediated disease or Syk-mediated condition is selected from the group consisting of nasal allergic disorders; rhinitis; and sinusitis.

2. The method of claim 1 wherein the allergic or inflammatory disease or other Syk-mediated disease or Syk-mediated condition is an allergic or inflammatory disease or other Syk-mediated disease or Syk-mediated condition of the nose.

3. The method of claim 2 wherein the composition is topically administered to the patient.

4. The method of claim 3 wherein the therapeutically effective amount of the compound is 0.00001-5% (w/v).

5. The method of claim 4 wherein the therapeutically effective amount of the compound is 0.0001-0.5% (w/v).

6. The method of claim 2 wherein the composition is topically administered to the nose of the patient.

7. The method of claim 6 wherein the allergic or inflammatory disease or other Syk-mediated disease or Syk-mediated condition is a nasal allergic disorder.

8. The method of claim 7 wherein the nasal allergic disorder is selected from the group consisting of allergic rhinitis and sinusitis.

* * * * *